United States Patent [19]

Kesling

[11] Patent Number: 4,897,036

[45] Date of Patent: Jan. 30, 1990

[54] TORQUING AUXILIARY

[75] Inventor: Peter C. Kesling, LaPorte, Ind.

[73] Assignee: TP Orthodontics, Inc., Westville, Ind.

[21] Appl. No.: 239,552

[22] Filed: Sep. 1, 1988

[51] Int. Cl.$^4$ ................................................ A61C 3/00
[52] U.S. Cl. ........................................ 433/18; 433/20
[58] Field of Search ................. 433/8, 16, 20, 22, 9, 433/18, 24

[56] References Cited

U.S. PATENT DOCUMENTS

| | | | |
|---|---|---|---|
| 4,353,692 | 10/1982 | Karrakussoglu | 433/16 |
| 4,424,033 | 1/1984 | Wool | 433/20 |
| 4,676,747 | 6/1987 | Kesling | 433/18 |
| 4,818,226 | 4/1989 | Berendt et al. | 433/20 |

*Primary Examiner*—Cary E. Stone
*Attorney, Agent, or Firm*—Lloyd L. Zickert

[57] ABSTRACT

An improved torquing appliance for use with any orthodontic treatment technique to apply either palatal or labial root torquing forces to any one or more teeth. The auxiliary is in the form of an arcuate wire of highly resilient material such that it will not take a permanent set in the normal range of activation but will tend to return to its passive state, and which includes a generally rectangular in cross section shape with one side shaped to partially receive in recessed relation a main archwire.

18 Claims, 2 Drawing Sheets

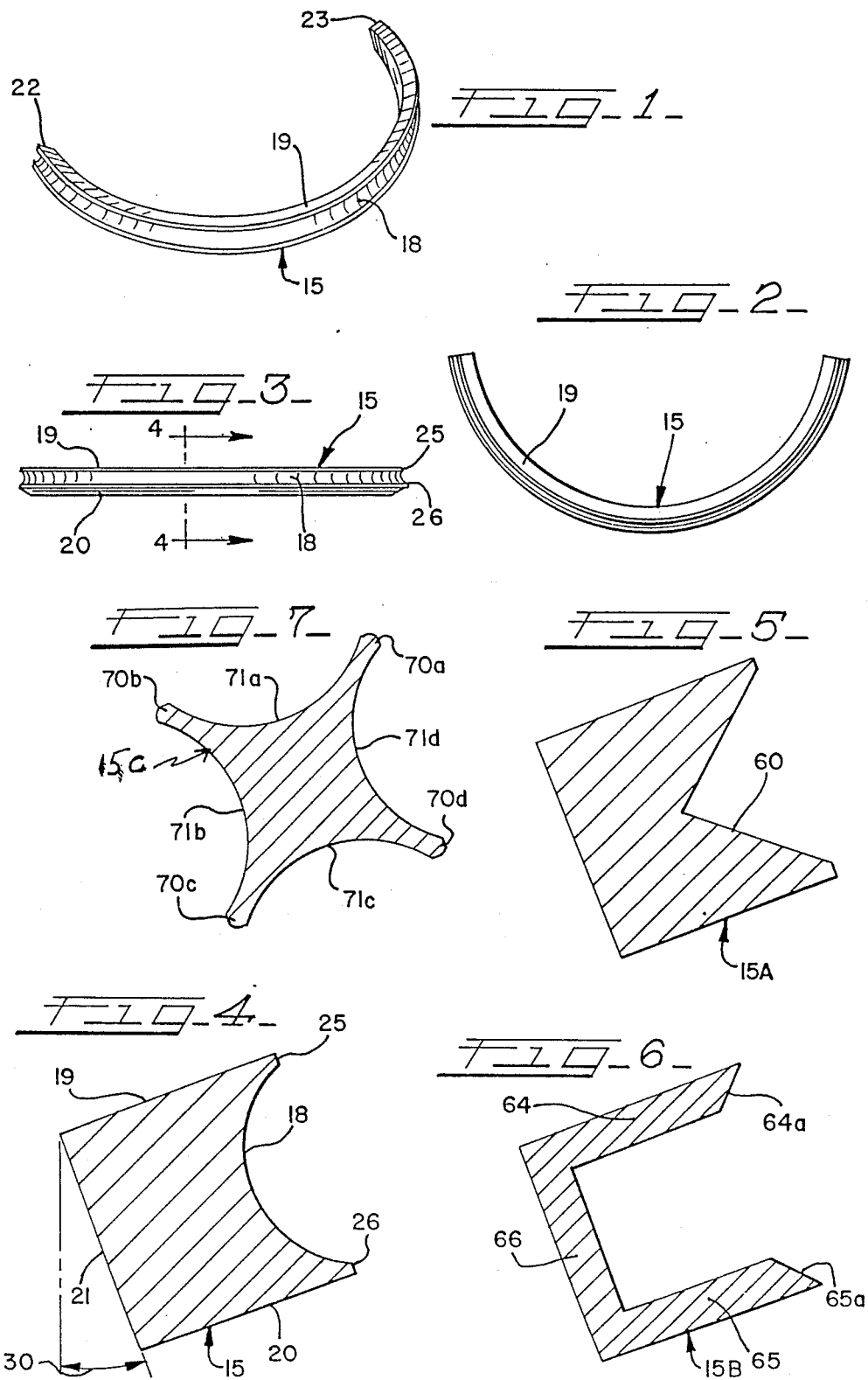

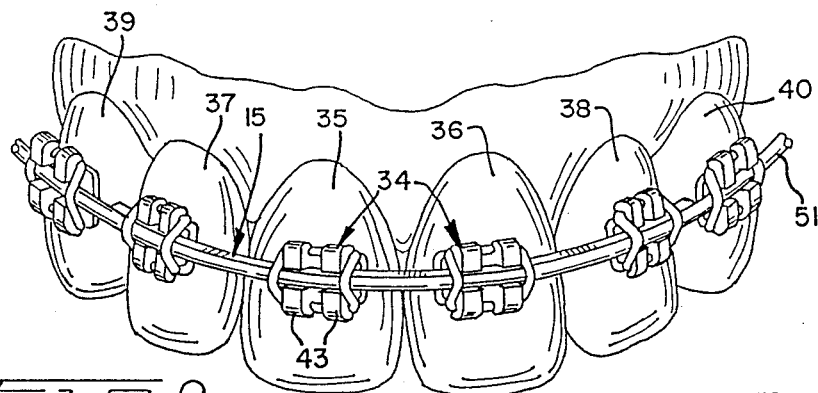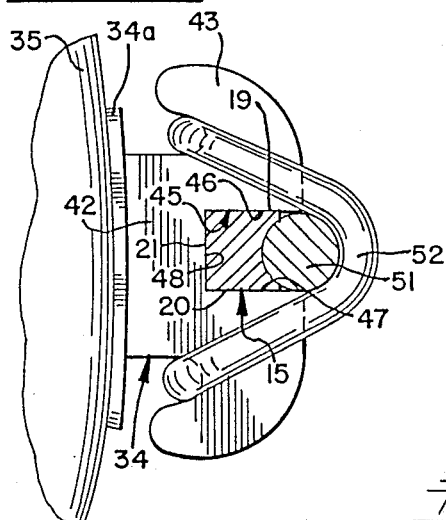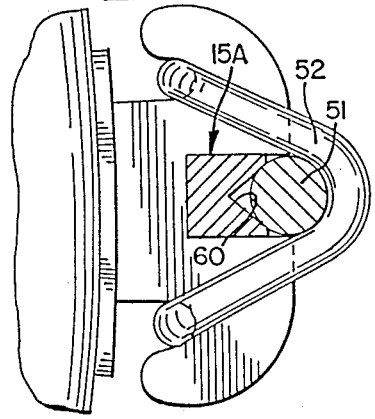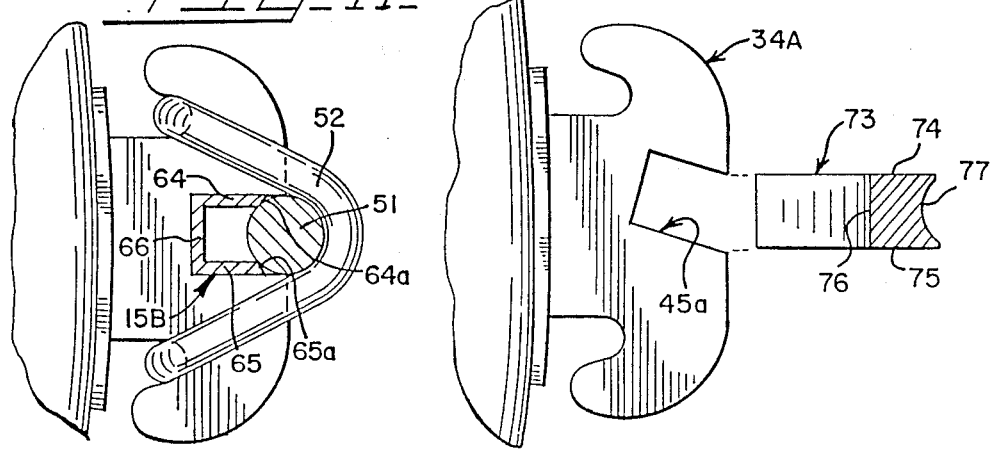

TORQUING AUXILIARY

This invention relates in general to an orthodontic appliance, and more particularly to an improved torquing auxiliary for applying torquing forces to teeth during orthodontic treatment, and still more particularly to an improved torquing auxiliary having a cross section of sufficient shape and size such as to prevent the auxiliary from turning in the archwire slot, and still more particularly to an auxiliary having a face that is configured to receive a portion of the main archwire and minimize labial protrusion.

BACKGROUND OF THE INVENTION

Heretofore, most torquing auxiliaries have been in the form of round in cross section wire that is arcuately configured and provided with loops that align with and bear against selected teeth and/or brackets to apply the torquing forces where the auxiliary is secured to a plurality of brackets. It has also been heretofore known to provide torquing springs that are anchored to an archwire and include a loop for engagement with a tooth to apply a torquing force. These torquing auxiliaries have been capable of providing either palatal or labial root torquing forces, but in all cases they have defined food traps which are difficult to clean, thereby adversely affecting mouth hygiene. Additionally, the loops detract from the aesthetics of an orthodontic system. Moreover, they quite often require reactivation or adjustment during the period of their use, and they require special skills for proper handling.

It has also been known to provide a torquing auxiliary which enhances the mouth hygiene of a person by minimizing food traps, thereby making it easier for a patient to keep the teeth clean. Such an auxiliary is disclosed in U.S. Pat. No. 4,676,747, which is assigned to the assignee of the present application. However, this auxiliary is not sized to reliably prevent turning in the archwire slot, nor does this auxiliary have a shape that will at least partially accommodate a part of the main archwire to minimize labial protrusion.

SUMMARY OF THE INVENTION

The present invention obviates the disadvantages heretofore encountered in torquing auxiliaries particularly in that it is free of vertical loops like the auxiliary in the above identified patent. In addition to having the advantages of the auxiliary in the above patent, the present invention is formed to provide the necessary amount of engagement with the archwire slot so as to prevent turning of the auxiliary wire in the slot while minimizing labial protrusion. This is accomplished by increasing the labiolingual depth of the auxiliary and providing a recess in the labial face for at least partially receiving the main archwire. The auxiliary of the present invention can be used with any type of orthodontic system and is easily adaptable for use with the Begg light wire technique and the various edgewise techniques. It also facilitates the use of uprighting springs which can more easily slide along the archwires and be more easily placed because of the absence of loops.

The auxiliary of the present invention is made of a wire that will not deform when normally activated and will always tend to resume its original passive shape. Thus, the wire is preferably made of highly resilient or flexible material such as a nickel titanium alloy, a beta titanium alloy, or any other highly flexible stainless steel alloy. It may be made of plastic with or without a metal core. The wire may be solid, twisted or braided and will have at least a portion that has a cross section to coact with a bracket to apply a torquing force. While the auxiliary of the present invention is primarily intended for applying torquing forces to the anterior teeth, it could be used to apply a torquing force to posterior teeth. It also could be used to torque only a single tooth or simultaneously a plurality of teeth. The word "rectangular" as used herein is intended to cover wire of both the typical rectangular or square cross sections.

The auxiliary of the present invention is used by first placing it in the archwire slot and then thereafter placing the main archwire in engagement with the labial face of the auxiliary. Suitable means is then used to locate both the auxiliary and the main archwire to the bracket such as by a pin or suitable ligature.

It is therefore an object of the present invention to provide a new and improved torquing auxiliary that is configured so that it will not turn or twist in an archwire slot when properly secured to a bracket and which, together with the main archwire, minimizes protrusion from the bracket.

It is a further object of the present invention to provide a torquing auxiliary that is configured to be first received in an archwire slot and thereafter engaging a main archwire that would be partially received within the slot.

It is therefore an object of the present invention to provide an improved torquing auxiliary that is devoid of loops and therefore more aesthetically desirable than an auxiliary having loops, and which makes it easier for a patient to maintain teeth cleanliness.

Another object of the present invention is in the provision of an improved torquing auxiliary for applying torquing forces to any of the teeth which is economical to manufacture, and easy to use and mount in a patient's mouth.

A still further object of the present invention is to provide an improved torquing auxiliary that is devoid of any loops and which can be used to apply a torquing force to one or more teeth directly through the brackets.

A still further object of the present invention is in the provision of a improved torquing auxiliary in the form of an arcuately formed length of wire of a highly resilient nature and which when mounted avoids the necessity for adjustment during its use for applying torquing forces.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of one embodiment of the torquing auxiliary of the present invention;

FIG. 2 is a top plan view of the torquing auxiliary of FIG. 1;

FIG. 3 is a front elevational or labial view of the auxiliary of FIG. 1;

FIG. 4 is a greatly enlarged transverse sectional view taken substantially along line 4—4 of FIG. 3;

FIG. 5 is a view like FIG. 4 but showing a modified recess in the labial face;

FIG. 6 is a view like FIG. 4 but showing a still further modification of the cross-sectional configuration of the auxiliary according to the invention;

FIG. 7 is a view like FIG. 4 but showing a still further modification of the cross-sectional configuration of the auxiliary according to the invention;

FIG. 8 is a front perspective view of anterior teeth having brackets and having the torquing auxiliary of the invention and a main archwire mounted on the brackets and particularly including the embodiment of FIGS. 1 to 4;

FIG. 9 is a greatly enlarged end or side elevational view of a bracket mounted on a fragmentary portion of a tooth and showing the torquing auxiliary of the embodiment of FIGS. 1 to 4 in association with a main round archwire as mounted on the bracket;

FIG. 10 is a view similar to FIG. 8 but showing the modified shape of the embodiment of FIG. 5;

FIG. 11 is a view similar to FIG. 8 but showing the modified shape of the auxiliary as shown in FIG. 6; and FIG. 12 is a greatly enlarged end or side elevational view of a bracket mounted on a fragmentary portion of a tooth and differing from the brackets shown in FIGS. 8 to 11 in that the archwire slot has built-in torque and also showing in exploded relation to the bracket the form of auxiliary that would be designed for this bracket, it being appreciated that the auxiliary is shown in a vertical sectional view taken approximately through the midline of the auxiliary.

DESCRIPTION OF THE INVENTION

The torquing auxiliary of the present invention is in the form of an arcuate wire of a length for applying a torquing force generally to one or more of the anterior teeth, although it could be used to apply torquing forces to any of the posterior teeth. While illustrated only in connection with applying torquing forces to the upper teeth, it will be appreciated that it is likewise useful for applying such forces to the lower teeth. Further, while illustrated in mounted relation only at the labial of the teeth, it could be used lingually in a lingual system. In all cases the wire is of a material that is highly resilient so that it can be activated without distorting the wire whereby it will tend to return to its normal passive state. It is the tendency to return from the activated to the passive state that causes the torquing forces to be applied to the teeth. Mounting the auxiliary on the teeth automatically activates the auxiliary, and unlike heretofore known auxiliaries of all round wire and having loops that may need adjusting, no adjustments are needed during its use.

While the wire may be made of any suitable highly resilient material having the desired memory characteristics, nickel titanium alloy has been found to be quite satisfactory. The object of the auxiliary is to apply light torquing forces to effect the suitable torquing of one or more teeth in accordance with a prescribed treatment plan. With respect to the upper teeth, the forces will be either palatal root torquing or labial root torquing. With respect to the lower teeth, the torquing forces for anterior teeth will be either lingual root torquing or labial root torquing.

It will be appreciated that the torquing auxiliary of the present invention will be of such a length that it will be secured to a plurality of brackets so that it can apply the proper torquing forces to the desired teeth. As with the torquing auxiliary in the aforesaid patent, portions of the auxiliary of the present invention may be formed so as to connect to selected teeth without applying any torquing forces. In this respect, the non-torquing portions would be preferably round in configuration so as not to apply torquing forces to the brackets engaged by the round portions. Those portions having generally rectangular cross section would apply torque to the brackets to which they are connected. It will be appreciated that the torquing auxiliary of the invention can be used most effectively and efficiently in combination with a round main archwire as illustrated in the drawings in either the Begg or edgewise technique.

It will be understood herein that a torquing force is one that intends to move a tooth about a mesiodistal axis toward a predetermined axial inclination from the vertical. Thus, the long axis of the clinical crown will be disposed at a desirable inclination. As above mentioned, the auxiliary is made from a suitable wire having the ability to flex upon being stressed, without deforming, and return to its passive state. Thus, when mounted in the mouth, it will be activated to apply the desired torquing force. In its free or passive state, as mentioned, it will be arcuate between its ends; while in its activated state, it will also be arcuate but twisted from its passive state position such as to apply a torquing force.

An important feature of the torquing auxiliary of the invention is that it does not include any loops as have been present in heretofore known torquing auxiliaries since it is well known that such loops become food traps that are difficult to clean and therefore adversely affect the mouth hygiene. Additionally, such loops may cause injury to the soft tissues of the mouth. It is also known that more adjustments are usually needed when using an auxiliary with loops. Thus, the auxiliary of the present invention, being devoid of loops, obviates these problems. Additionally, the present invention enhances the aesthetics of an orthodontic system by eliminating unsightly loops and facilitates the ability for springs to be positioned along an archwire.

Referring now to the drawings, and particularly to the embodiment shown in FIGS. 1 to 4 and in mounted relation on brackets in FIG. 7, the auxiliary of the invention, generally designated by the numeral 15, is, in its passive state as seen in FIGS. 1 to 4, arcuate in shape and configured so that when it is mounted on the brackets it will exert a torquing force on those teeth that are associated with the brackets. The auxiliary is in the form of a wire having a cross-sectional shape that is rectangular or square or mates with a rectangular slot and may be of any length desired in order to cover a desired number of teeth on an arch.

The auxiliary includes a front or labial face or side 18, an upper flat side 19, a lower flat side 20, and a flat back side 21. The sides need not be flat as long as the wire non-rotationally mates with the archwire slot. The auxiliary terminates at distal ends 22 and 23. Opposing top and bottom sides 19 and 20 are parallel to each other and the back side 21 extends perpendicular to the parallel sides. The front face 18 is curvately formed or more particularly cylindrically formed and of a radius that is equal to or greater than that of the archwire to be used in conjunction with the auxiliary. Face 18 defines the surface against which the archwire will engage when the auxiliary is properly mounted in the brackets, as seen in FIG. 7. At the opposite ends of the front face 18, a plane extending through edges 25 and 26 is arranged in substantial parallel relation with the back side 21. A plane through the back side 21 defines a reference plane for the auxiliary and is inclined to the vertical a predetermined angle 30. Preferably, this angle is about 20 degrees. While the back side is flat, it can be appreciated that it may have another shape.

Auxiliary 15 is illustrated in mounted relation on standard twin tie wing edgewise brackets, as seen particularly in FIGS. 7 and 8. When mounting the auxiliary in the brackets, it is necessary to stress the auxiliary in order for it to be properly seated in the archwire slots of the brackets, thereby causing it to exert a torquing force on the teeth.

The edgewise brackets illustrated are generally indicated by the numeral 34 and suitably secured to a pad 34a which is in turn suitably bonded to the labial face of the teeth. For purposes of illustrating the invention, as seen in FIG. 7, brackets 34 are mounted on centrals 35 and 36, laterals 37 and 38, and cuspids 39 and 40. Each bracket includes a base 42, twin tie wings 43, and a horizontally opening rectangular archwire slot 45. The archwire slot includes an upper wall 46, a lower wall 47, and a back wall 48. As seen particularly in FIG. 8, when the auxiliary is mounted in the archwire slots, the upper side 19 of the auxiliary mates with the upper wall 46 of the archwire slot, while the lower side 20 of the auxiliary mates with the lower wall 47 of the slot. The back side 21 of the auxiliary fits against the back wall 48 of the archwire slot. Here, it can be seen that the auxiliary is first placed in the archwire slot and thereafter the main round archwire 51 is placed in the front recess of the auxiliary such that the archwire mates with the labial side 18 of the auxiliary. Thereafter, the auxiliary and the archwire are connected to the bracket by means of a standard elastic ligature 52. Other types of ligatures may also be used in place of elastic ligatures.

It can be seen, particularly by FIG. 8, that the labiolingual depth of the auxiliary is substantially more than one-half the labiolingual depth of the archwire slot, although of such a length that about half of the cross section of the main archwire 51 will be received in the archwire slot. This is preferable in that it provides a more reliable engagement between the main archwire and the bracket.

By substantially filling the archwire slot, relative turning of the auxiliary in the slot is prevented.

The auxiliary 15 as mounted on the upper teeth, shown in FIG. 7, is configured to exert a palatal root torque to the teeth. If it were desired to exert a labial root torque to the teeth, it would be necessary to configure the torquing auxiliary in an opposite manner where the cross section of the auxiliary, as seen in FIG. 4, would be rotated clockwise 40 degrees so that a line going through the back side of the auxiliary would be tilted in an opposite direction away from the vertical. As shown in FIG. 4, the auxiliary is tilted counterclockwise from the vertical to produce lingual root torque, while if labial root torque would be desired, it would need to be tilted clockwise from the vertical.

As seen in FIG. 7, the length of the auxiliary is such as to terminate between the laterals and the cuspids, as normally the torquing force is applied to the centrals and laterals only. If it were desired to provide additional activation, extensions that are round in cross section could be added to the distal ends of the auxiliary for being anchored in the brackets of the cuspids. By being round, there would be a rotational connection between the auxiliary and the teeth as is fully described in the above mentioned patent.

Installing the auxiliary would involve first inserting the auxiliary in the brackets of the centrals by raising the distal ends of the auxiliary gingivally or above the archwire slot plane. Thereafter, those ends would be pushed downwardly so that the corresponding portions of the auxiliary could then be inserted into the brackets on the laterals. Following the mounting of the main round archwire and the ligating of the archwire and the torquing auxiliary to the brackets, the installation of the torquing auxiliary is complete and the auxiliary will be activated so as to apply a torquing force.

It will be appreciated that if the torquing auxiliary is configured to apply a labial root torque when the auxiliary is mounted in the brackets of the centrals, the distal ends will extend incisally from the plane of the archwire slot and then need to be raised to the plane and inserted in the brackets of the laterals before the mounting of the main archwire and the ligating of the archwire and the auxiliary to the brackets. The auxiliary will then exert a labial root torque force on the teeth.

While not illustrated, it can be appreciated that the auxiliary of the invention can be used in a ribbon arch bracket that is used in the Begg technique and which is illustrated in the above identified patent.

It will be appreciated that it is not necessary to form any loops in the auxiliary to obtain the necessary and desired torquing action, and since the auxiliary is rectangular in cross section throughout its length, it will apply a torquing force to all of the brackets to which it is connected against relative rotational movement. Fitting the rectangular auxiliary in the rectangular archwire slots connects the auxiliary to the brackets against relative rotational movement so that the force of the auxiliary is imparted to the brackets and ultimately to the teeth on which the brackets are mounted.

Another embodiment of the invention is shown in FIGS. 5 and 9 which only differs in the shape of the labial face that mates with the main archwire. This embodiment, generally designated by the numeral 15A, has a labial face 60 that is V-shaped. As seen in FIG. 9, the main round archwire 51 engages the V-shaped face at the upper end or lower ends. Other than the shape of the labial face, it will be appreciated that the auxiliary 15A operates in the identical fashion as the auxiliary 15.

Another cross-sectional form of the auxiliary is shown in FIGS. 6 and 10, wherein the auxiliary is channel-shaped. It is provided with the same external top, bottom and back sides that engage the archwire slot, but is open at the labial side. This embodiment, generally designated by the numeral 15B, being in the cross-sectional form of a channel, includes upper and lower legs 64 and 65 and an interconnecting rear leg 66. The upper and lower legs can be beveled at their free ends 64a and 65a, as shown in FIG. 10, so as to facilitate the mating relation with the round archwire 51. As the round archwire sits in fitted relation with the beveled surfaces 64a and 65a, the archwire will tend to move farther into the archwire slot. Otherwise, auxiliary 15B operates in the identical fashion as auxiliaries 15 and 15A.

A further modification of the auxiliary is shown in FIG. 7 which would operate in the same manner as the auxiliaries of FIGS. 4, 5 and 6 but differ only in the crosssectional configuration. This embodiment is generally designated as 15C and cross-sectionally is generally starshaped, having four symmetrically arranged points 70a, 70b, 70c, 70d between which are concave faces 71a, 71b, 71c, 71d. Points 70a and 70b lie in a plane that is parallel to points 70c and 70d and which are perpendicular to a plane in which points 70b and 70c will lie. Similarly, a plane through points 70a and 70d would be parallel to the plane through points 70b and 70c such that the cross-sectional shape of the auxiliary will mate with the rectangular archwire slot of a bracket. This configuration illustrates that the faces of the auxiliary which oppose the walls of the archwire slot need not be flat, as shown in the embodiments of FIGS. 4, 5 and 6, in order to practice the present invention.

It is well known that edgewise brackets are available in pre-torqued archwire slots, and it is to be understood that the auxiliary wire of the present invention may be configured to provide a torquing force in such a bracket while still providing the advantages over the auxiliary disclosed in U.S. Pat. No. 4,676,747. Particularly, the auxiliary of the invention precludes turning or twisting in the archwire slot and also minimizes protrusion of the main archwire from the bracket. The bracket shown in FIG. 12 and generally indicated by the numeral 34A includes such a pre-torqued archwire slot 45a for use with this type of bracket. The auxiliary would be formed where the back face is perpendicular. More particularly, this auxiliary is generally indicated by the numeral 73 and includes top and bottom parallel arranged sides or faces 74 and 75 and a back face or backside 76 that extends perpendicular to the sides 74 and 75. The front face or side 77 is concave to matingly receive the main archwire. Once this auxiliary is placed and tied to the brackets on the arch, it will produce a palatal root-torquing force on the bracket 34A. It will be noted that the labiolingual depth of auxiliary 73 is, like the other embodiments, substantially more than one-half of the labiolingual depth of the archwire slot 45a and that the main archwire is partially received within the archwire slot, as illustrated in the other embodiments.

It will be understood that modifications and variations may be effected without departing from the scope of the novel concepts of the present invention, but it is understood that this application is to be limited only by the scope of the appended claims.

The invention is hereby claimed as follows:

1. In combination with an orthodontic system for an arch of a person including a plurality of brackets mounted on the teeth of the arch and having generally aligned rectangular arch wire slots, a torquing auxiliary received in said archwire slots and attached to a plurality of said brackets on a curved segment of the arch for applying a torquing force to a tooth, a main archwire at least partially received in said archwire slots attached to all of said brackets, said auxiliary comprising a wire of highly resilient material such that it will not easily permanently deform when stressed from its passive or unstressed state and when stressed will tend to return to its passive state, said auxiliary wire being arcuate along its length in its passive or unstressed state and devoid of any loops and having a cross section therealong mating with the archwire slot against relative rotation where it is attached to at least one bracket and stressed when attached to adjacent brackets to apply torque to the tooth on which the bracket is mounted against rotation, said auxiliary wire having opposed generally parallel flat surfaces for engaging opposed parallel sides of the archwire slot and one of the other surfaces having a recess shaped to receive at least a portion of the main archwire so as to minimize protrusion from the bracket, whereby the auxiliary is passive in one position prior to mounting on the brackets and then turned about fifteen to ninety degrees from the passive state and stressed and arcuately formed on the curved segment of the arch in a different dimension than when in its passive state to then be attached to the brackets in the stressed state thereby activating the auxiliary to apply torque to the bracket or brackets to which it is mounted against relative rotation.

2. The auxiliary wire of claim 1, wherein said one surface is shaped to receive a round main archwire.

3. The auxiliary wire of claim 2, wherein said one surface is concave to matingly receive a round main archwire.

4. The auxiliary wire of claim 2, wherein said one surface is V-shaped.

5. The auxiliary wire of claim 2, wherein said one surface includes spaced edges engageable by the main archwire.

6. The combination of claim 1, wherein said auxiliary wire is channel shaped in cross section with the open side adapted to face outwardly of the archwire slot and mate with the archwire.

7. The auxiliary wire of claim 1, which is starshaped in cross section.

8. An improved torquing auxiliary for use in ribbon arch or edgewise brackets on a curved segment of the arch and having a rectangular archwire slot with opposed parallel sides, a bottom side and an open side opposite the bottom side, said auxiliary comprising a wire of highly resilient material such that it will not easily permanently deform when stressed from its passive or unstressed state and when stressed will tend to return to its passive state, said auxiliary wire being arcuate along its length in its passive or unstressed state and devoid of any loops and having a cross section therealong mating with the archwire slot against relative rotation therewith where it is attached to at least one bracket and stressed when pulled to the level of the arch and attached to the adjacent brackets to apply torque to the tooth on which the bracket is mounted against rotation, said auxiliary adapted to be used in conjunction with a main archwire where the auxiliary is first received in the archwire slots and the main archwire is placed in abutting relation to the auxiliary wire and at least partially received in the slot, said auxiliary wire having opposed parallel flat surfaces for engaging opposed parallel sides of the archwire slot and the surface at the open end of the archwire slot having a recess to receive at least a portion of the main archwire so as to minimize protrusion from the bracket, whereby the surface of the auxiliary wire opposite the surface receiving the archwire is inclined from the vertical when in its passive state prior to being mounted on the brackets and resting on a flat horizontal surface.

9. The auxiliary of claim 8, wherein said archwire receiving side of the auxiliary wire is inclined about twenty degrees from the vertical.

10. The auxiliary of claim 9, wherein the archwire receiving side of the auxiliary wire is arcuately shaped to substantially matingly receive the archwire.

11. The auxiliary of claim 9, wherein the archwire receiving side of the auxiliary wire is concave.

12. The auxiliary of claim 9, wherein the archwire receiving side of the auxiliary wire is V-shaped.

13. The auxiliary of claim 9, wherein the archwire receiving side of the auxiliary wire is generally open.

14. The auxiliary of claim 8, wherein the auxiliary wire is channel-shaped in cross section with the open side mating with the main archwire.

15. The auxiliary of claim 8, wherein the auxiliary is formed for use in an edgewise bracket.

16. An improved torquing auxiliary for use in ribbon arch or edgewise brackets on a curved segment of the arch and having a rectangular archwire slot with opposed parallel sides, a bottom side and an open side opposite the bottom side, said auxiliary comprising a wire of highly resilient material such that it will not easily permanently deform when stressed from its passive or unstressed state and when stressed will tend to return to its passive state, said auxiliary wire being arcuate along its length in its passive or unstressed state and devoid of any loops and having a cross section therealong mating with the archwire slot against relative rotation therewith where it is attached to at least one bracket and stressed when attached to the adjacent brackets to apply torque to the tooth on which said one bracket is mounted, said auxiliary adapted to be used in conjunction with a main archwire where the auxiliary is first received in the archwire slots and the main archwire is placed in abutting relation to the auxiliary wire and at least partially received in the slot, said auxiliary wire being sized and shaped to have a depth of substantially more than one-half the archwire slot and to coact with the main archwire to minimize its protrusion from the outer face of the bracket.

17. The auxiliary wire of claim 16, which is formed for a bracket having a non-torqued archwire slot and in its passive state a plane through the face adapted to be opposite the base of the archwire slot is inclined from the vertical when the auxiliary wire is resting on a flat horizontal surface.

18. The auxiliary wire of claim 16, which is formed for a bracket having a pre-torqued archwire slot and in its passive state a plane through the face adapted to be opposite the base of the archwire slot extends vertically when the auxiliary wire is resting on a flat horizontal surface.

* * * * *